(12) United States Patent
Fornarelli

(10) Patent No.: US 11,395,372 B2
(45) Date of Patent: Jul. 19, 2022

(54) VAPORIZATION DEVICE, A CHARGING ADAPTOR FOR A DISPOSABLE VAPORIZATION DEVICE, AND A KIT

(71) Applicant: DB Innovation Inc., Chicago, IL (US)

(72) Inventor: Thomas Fornarelli, Chicago, IL (US)

(73) Assignee: DB INNOVATION INC., Chicago, IL (US)

( * ) Notice: Subject to any disclaimer, the term of this patent is extended or adjusted under 35 U.S.C. 154(b) by 68 days.

(21) Appl. No.: 16/157,598

(22) Filed: Oct. 11, 2018

(65) Prior Publication Data

US 2019/0037928 A1    Feb. 7, 2019

Related U.S. Application Data

(63) Continuation-in-part of application No. 15/181,323, filed on Jun. 13, 2016, now Pat. No. 10,111,468.

(51) Int. Cl.
| | |
|---|---|
| A24F 13/00 | (2006.01) |
| A24F 17/00 | (2006.01) |
| A24F 25/00 | (2006.01) |
| H05B 1/02 | (2006.01) |
| A24F 7/02 | (2006.01) |
| A24F 21/00 | (2006.01) |
| H05B 3/42 | (2006.01) |
| A61M 11/04 | (2006.01) |

(Continued)

(52) U.S. Cl.
CPC ............ *H05B 1/0227* (2013.01); *A24F 7/02* (2013.01); *A24F 21/00* (2013.01); *A24F 40/30* (2020.01); *A24F 40/40* (2020.01); *A61M 11/042* (2014.02); *A61M 15/0003* (2014.02); *A61M 15/06* (2013.01); *H05B 3/42* (2013.01); *A24F 40/10* (2020.01); *A61M 2016/0021* (2013.01); *A61M 2205/3368* (2013.01); *A61M 2205/3553* (2013.01); *A61M 2205/3584* (2013.01); *A61M 2205/3592* (2013.01); *A61M 2205/52* (2013.01); *A61M 2205/586* (2013.01); *A61M 2205/8206* (2013.01); *A61M 2205/8243* (2013.01)

(58) Field of Classification Search
CPC ..................................................... A24F 47/008
USPC .......................................... 131/329; 439/484
See application file for complete search history.

(56) References Cited

U.S. PATENT DOCUMENTS

| | | | | |
|---|---|---|---|---|
| 5,971,801 A | * | 10/1999 | Kato | ................ H01R 13/62933 439/157 |
| 10,412,785 B1 | * | 9/2019 | Schwartz | ................. H05B 3/06 |

(Continued)

FOREIGN PATENT DOCUMENTS

| | | |
|---|---|---|
| WO | 2014/066730 A1 | 5/2014 |
| WO | 2015/149647 A1 | 10/2015 |

OTHER PUBLICATIONS

European Patent Office, Munich, Germany, Date: Feb. 13, 2020, PCT/US2017037206, Applicant: DB Innovation Inc., Communication, European Search Report.

(Continued)

*Primary Examiner* — Abdullah A Riyami
*Assistant Examiner* — Thang H Nguyen
(74) *Attorney, Agent, or Firm* — Flener IP & Business Law; Zareefa B. Flener

(57) ABSTRACT

A vaporization device comprises a body configured to house at least one pen in a cavity inside the body. The body comprises a bottom surface and a top surface, and a grip is releasably attached to the bottom surface.

12 Claims, 10 Drawing Sheets

(51) Int. Cl.
  *A61M 15/06* (2006.01)
  *A61M 15/00* (2006.01)
  *A24F 40/30* (2020.01)
  *A24F 40/40* (2020.01)
  *A61M 16/00* (2006.01)
  *A24F 40/10* (2020.01)

(56) References Cited

U.S. PATENT DOCUMENTS

| | | | | |
|---|---|---|---|---|
| 2006/0233591 A1* | 10/2006 | Dietz | ............... | B43K 29/02 |
| | | | | 401/131 |
| 2009/0117776 A1* | 5/2009 | Kuo | ............... | H01R 13/6335 |
| | | | | 439/484 |
| 2009/0314225 A1* | 12/2009 | Moran | ............... | A01K 1/04 |
| | | | | 119/786 |
| 2014/0060527 A1* | 3/2014 | Liu | ............... | A24F 40/30 |
| | | | | 128/202.21 |
| 2014/0060554 A1* | 3/2014 | Collett | ............... | A24F 40/30 |
| | | | | 392/386 |
| 2014/0261488 A1* | 9/2014 | Tucker | ............... | A24F 40/50 |
| | | | | 131/328 |
| 2015/0053217 A1* | 2/2015 | Steingraber | ............... | A24F 40/50 |
| | | | | 131/329 |
| 2015/0090253 A1* | 4/2015 | Farrow | ............... | A61M 15/0003 |
| | | | | 128/200.14 |
| 2015/0180172 A1* | 6/2015 | Hiscoke | ............... | H01R 13/6272 |
| | | | | 439/153 |
| 2015/0245666 A1* | 9/2015 | Memari | ............... | H02J 7/0042 |
| | | | | 131/329 |
| 2016/0183592 A1* | 6/2016 | Liu | ............... | A24F 40/50 |
| | | | | 131/329 |
| 2016/0198763 A1* | 7/2016 | Adkins | ............... | A24F 15/01 |
| | | | | 206/268 |
| 2016/0345628 A1* | 12/2016 | Sabet | ............... | A24F 40/95 |
| 2017/0043910 A1* | 2/2017 | Hopps | ............... | A24F 15/12 |
| 2017/0049155 A1* | 2/2017 | Liu | ............... | H05B 1/0244 |
| 2019/0029319 A1* | 1/2019 | Moorman | ............... | A24F 9/02 |

OTHER PUBLICATIONS

Soulohm: "The Hell's Gate V2 by Yep—Review", Youtube, Mar. 30, 2016, URL: https://www.youtube.com/watch?v=4cn7kPxXFCk.

\* cited by examiner

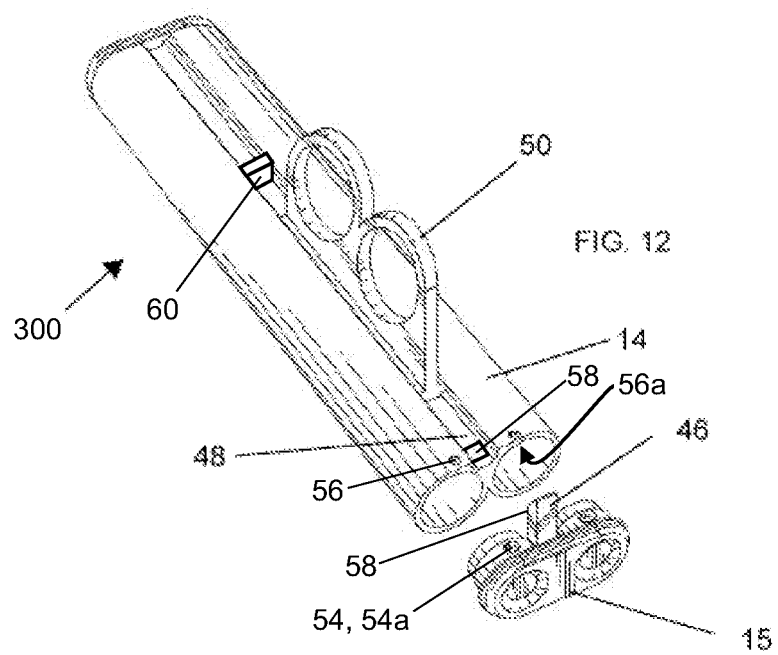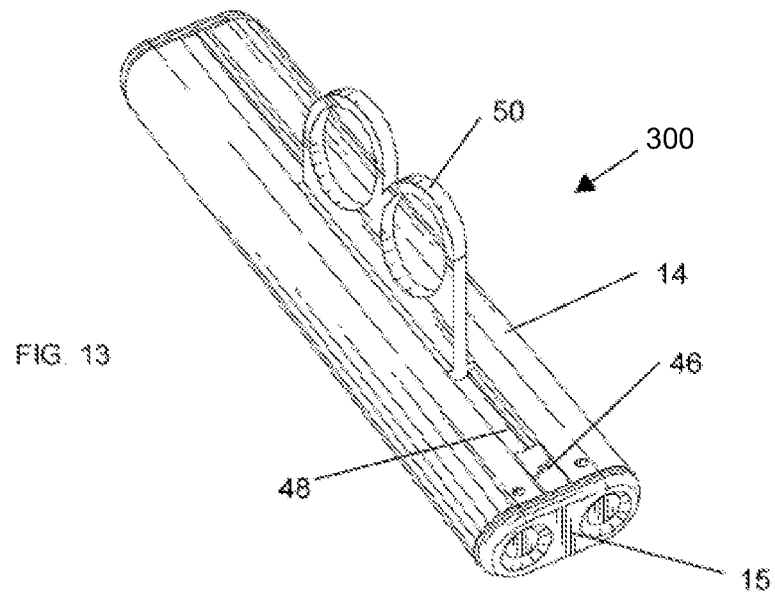

VAPORIZATION DEVICE, A CHARGING ADAPTOR FOR A DISPOSABLE VAPORIZATION DEVICE, AND A KIT

CROSS REFERENCE TO RELATED APPLICATIONS

This application is a continuation-in-part of application Ser. No. 15/181,323 filed Jun. 13, 2016, the contents of which are incorporated by reference in their entirety, as if fully restated herein.

FIELD OF THE INVENTION

The present invention relates to a vaporization device. More specifically, the present invention relates to a vaporization device having a detachable handle or grip, a charging adaptor for a disposable vaporization device, and a kit.

BACKGROUND

Vaporization devices include various common components including a coil, a vaporization chamber, a battery, a mouthpiece, and a reservoir. The reservoir is filled with electronic liquid ("e-liquid") which can be composed of essential oils and/or other chemicals such as nicotine and/or cannabinoids. A wick acts as a bridge between the e-liquid in the reservoir and the vaporization chamber. It is the coil that plays a key element in vaping at the right temperature for the particular e-liquid as it is responsible for reaching a certain temperature and maintaining the same. Not enough heat means no vapor, too much heat and the coil could burn the e-liquid, and potentially produce toxins for inhalation.

A vaporizer pen works by heating the e-liquid to a specific temperature and then releasing its active substance/essential oils in the form of water vapor. By using this particular process, the plant materials are not burned, and this means that there is no combustion (emission of smoke or other toxic chemicals like carbon dioxide), unlike that of traditional smoking of tobacco and other dry herbs.

As a vape pen is portable, it must be properly charged to work. A lithium-ion battery is mostly used with cordless vaporizers, and these batteries can either be charged using a wall adapter, portable charging case, or a USB charger. Once the lithium-ion battery is fully charged, a device is ready to use. Some vape pens are disposable and not rechargeable. The battery in disposable pens can lose charge and not vaporize all of the e-liquid. The e-liquid that remains after the battery has lost charge is typically thrown away, the only solution being to purchase or acquire a brand-new pen.

Using a vaporizer pen involves inhaling directly through a mouthpiece on the device. Typically, sensors inside the pen sense the inhalation, for example, via a change in pressure, and signal the inhalation to internal circuitry that activates a heat source for the pen. The heat source heats the e-liquid in the pen to a specific temperature (below that of combustion/smoke) to produce vapor from the essential oils of the e-liquid.

The e-liquid that is often used with a vapor pen for vaporizing nicotine can come in a variety of strengths of nicotine, ranging from 0 to 36 mg, as compared to approximately 12 mg in a normal cigarette. Often vaporization pens are utilized to cut down on nicotine use, by moving from higher levels of nicotine to lower levels of nicotine, to eventually zero nicotine, while at the same time, achieving an enjoyable vaping experience by vaping hundreds of the available e-liquid flavors on the market. Vaporization pens can also be used to vaporize other substances including essential oils, THC, cannabinoids, and other plant-based substances.

Vaporizers work by using heating elements that heat up the chemicals or substances in the e-liquid to the point of boiling or vaporization, but not too hot otherwise there is a risk of burning the botanicals. Many portable vaporizers feature efficient heating systems with adjustable temperature settings to give greater freedom to get to the exact temperature preferred for unlocking particular benefits of the specific e-liquid.

When vaping marijuana, for example, vaping temperatures ranging from 175° C. to 190° C. tend to result in more sedative or relaxing effects, also depending in part on the strain of the plant involved. But, any temperature that goes beyond 230° C. renders the herbs to combustion. Many vaporization pens do not feature adjustable heat settings, and therefore, it is often more difficult to get the best result from a mix of different chemicals, and even from a single herb or essential oil due to the burning of some quickly at a particular temperature and dominating the flavor/effect. Each herb or plant can have hundreds of cannabinoids, each of which may have a unique boiling and vaporization temperature.

Tetrahydrocannabinol (THC) is more often vaped at a temperature of between about 155° C. to 160° C. It is perhaps the most essential and sought-after cannabinoid among medical and most especially recreational marijuana users. Taken in adequate doses, THC has been demonstrated to help alleviate symptoms of pain and other physical discomfort. Some studies have also shown that this cannabinoid protects brain cells and can even promote growth. Different cannabis strains contain varying levels of THC and proportions of other cannabinoids. For example, the *Sativa* varieties boast the highest amount of THC, while Indica ones contain more of the other health-giving cannabinoids than the more psychoactive THC.

Cannabidiol, otherwise known as CBD, has a vaping temperature of between about 160° C. to 180° C. This cannabinoid is as abundant as THC in any cannabis plant. And while the major controversies surrounding marijuana use actually focus on the effects of THC with all those reported highs and psychomotor impairments in large doses, CBD may arguably offer a more promising use of cannabis in the medical field.

Contrary to common perception, CBD is non-psychoactive, meaning that it does not interfere with your judgment or motor skills. Rather, and more importantly, are the therapeutic effects of CBD. These include the cannabinoid's anti-convulsant (suppresses epileptic seizures), anti-cancer (hampers the growth of tumor cells), anti-inflammatory and anti-oxidant properties (fights against neurodegenerative disorders such as Alzheimer's disease). Studies also show that CBD alleviates anxiety and depression.

Unlike THC, Cannabinol ("CBN"), with a vaping temperature of about 185° C. has the opposite effect of inducing sleep, making this a good drug for those suffering from insomnia. But beyond its sedative effects, CBN has also been found to combat methicillin-resistant *Staphylococcus aureus* (MRSA), a powerful bacteria that's been hard to eliminate because of its resistance to antibiotics. Cannabinol does not occur naturally in fresh cannabis. Instead, it becomes the byproduct formed as THC degrades over time.

Tobacco vaporizes at between about 120-150° C. (257-302° F.).

Of course, cannabis herb is not the only plant vaporized. Other herbs are also popular for vaping and offer soothing and relaxing sensations when vaporized and inhaled. In fact, many of these plants contain substances that have more subtle psychoactive effects.

For example, some preferred vaping temperatures for the following dry herbs are: eucalyptus, 266° F. (130° C.); hops, 309° F. (154° C.); chamomile, 374° F. (190° C.); lavender, 266° F. (130° C.); lemon balm, 288° F. (142° C.); sage, 374° F. (190° C.); thyme, 374° F. (190° C.). These temperatures provide aromatherapy benefits as well. These temperatures are also ideal for aromatherapy.

The composition of essential oils is typically complicated. Essential oils are constituted by terpenoid hydrocarbons, oxygenated terpenes and sesquiterpenes. They originate from the plant secondary metabolism and are responsible for their characteristic aroma. Although the essential oils have a great number of components, the ones of commercial interest are generally those composed of one or two major components, which provides them with accurate features. Nonetheless, in some cases, the minor components are also important because they might provide the oils with exquisite perfume, that is why this kind of material must be handled with care. The extraction, preservation and conditioning of such a material are very important in order not to alter its composition, and equally, when vaporized, effective temperatures should be maintained to get the most benefit from the same. Each essential oil has a different boiling point and contains a variety of different terpenes (which are the fragrance molecules)—and it is possible to experience a different flavor and effect from one temperature to the next.

This balance of and reaction between constituents is also what makes one oil more or less toxic than another. The proportion of a toxic constituent in one oil may be balanced by other constituents which make the potential toxin less significant and allow the oil to be useful in therapy.

E-liquid contains at least four ingredients including propylene glycol ("PG") and vegetable glycol ("VG"), nicotine and/or cannabis, and water. Propylene glycol is relatively thin in consistency, is runnier than the VG variety, and is more easily absorbed by the wick. The low density also lends itself to less build up on the heating element of the pen as fast as when thicker vegetable glycerin liquid is used. VG is a considerably thicker solution, compared to PG. On its own, VG has a slight sweet taste which also makes the e-liquid sweeter and the flavors a little difficult to detect. Although mixing e-liquid to create a personalized blend is becoming more common, it is not the easiest of tasks due to the different consistencies of PG, VG and water.

PG boils at 188° C. (370° F.) while VG boils at 290° C. (554° F.). Thus, vaping at 100% VG involves higher coil temperatures (water does not mitigate temps since it evaporates early).

As mentioned, vaporizing pens are not all provided with heat control mechanisms. With pens, a closed circuit, administered by a sensor, for instance, but not limited to, an air sensor or pressure sensor, in communication with the printed circuit board (PCB) and the battery, activates the heating element which then vaporizes the exposed herbs or nicotine in the e-liquid which are delivered to the vaporization chamber. There is no way to easily adjust the temperature in vaporizing pens. Some attempts to control a vaping temperature of a single e-liquid in a pen, which can contain many different chemicals with desired effects, have been proposed including pressing and holding an activation button (if it has one) down to heat the coil, releasing the button a few seconds after. Then pressing again and releasing again in a rhythmic sequence, thereby preventing the coil from operating at full capacity, and resulting in a slightly cooler temperature and even battery savings. Another proposal is for when not inhaling for a long time, turning the vaporizer off, rather than relying on the automatic shut-off mechanism of the device to save on battery and vapors. Other vaporizers are designed with an embedded heating element so that the herbs inside the chamber are not directly exposed, thus keeping the materials from burning.

Overheating a coil will burn the chemicals in an e-liquid such that at least the beneficial effects are not obtained, and at the most, the burned chemicals or even the wick can be toxic, harmful and have an unpleasant taste. It is difficult to mix different e-liquids for vaporization at least because different e-liquids have different viscosities and do not always easily mix; and e-liquids contain different herbs with different chemicals which, as mentioned above, have different temperatures of vaporization.

A device is needed, therefore, which can more completely vaporize a plurality of chemicals in a plurality of e-liquids at the same time, thereby providing a vaping experience which combines the effects of each component in a particular e-liquid at the same time, for both disposable and rechargeable pens.

SUMMARY OF THE INVENTION

According to one aspect of the invention, a vaporization device comprises a body configured to house at least one pen in a cavity inside the body. The body comprises a bottom surface and a top surface. A grip is releasably attached to the bottom surface of the body.

According to another aspect of the invention, a charging adapter for a disposable vaporization device comprises at least one battery and an inductive battery charger comprising a charging coil which creates magnetic flux lines when said charging coil is energized. A flat band is disposed in non-direct electrical contact with the inductive charger, the flat band being placed around the disposable vaporization device adjacent to at least one battery inside the disposable vaporization device, wherein the energy in said charging coil is inductively transferred from the inductive battery charger to the battery inside the vaporization device through the band.

According to a further aspect of the invention, a vaporization device comprises a body configured to house at least two pens. The body has a first end and an opposing second end, wherein the second end comprises a PCB that is operatively connected to each of the at least two pens and a sensor. A mouthpiece is adjacent and contiguous with the first end of the body, wherein the mouthpiece is provided with an aperture at a first end. The aperture extends into a vapor port which is operatively connected to a plurality of vaporization chambers at an end opposing the aperture. The at least two pens each have a battery, a plurality of vaporization chambers, and a reservoir. The battery is operatively connected to a PCB and the sensor. The PCB is operationally connected to a plurality of coils and each battery of each pen and configured to control a temperature of each coil in each one of a plurality of vaporization chambers. The plurality of vaporization chambers each houses a coil for vaporization operatively connected to the PCB and a battery for controlling the temperature of the coils to heat at a uniform temperature across the plurality of coils. The vaporization device further comprises at least one microprocessor and at least one airflow aperture.

According to yet another aspect of the invention, a kit comprises a vaporization device, a charging cable adapted to electrically connect the vaporization device to a charger, a rechargeable case, at least one battery, and a plurality of tanks filled with vaporizable substances.

BRIEF DESCRIPTION OF THE DRAWINGS

FIG. 12 illustrates an exploded bottom view of an embodiment of the device in accordance with the principles of the present invention;

FIG. 13 illustrates a bottom view of the embodiment of FIG. 12;

Other aspects and advantages of the present invention will become apparent upon consideration of the following detailed description, wherein similar structures have similar reference numerals.

DETAILED DESCRIPTION

The following detailed embodiments presented herein are for illustrative purposes. That is, these detailed embodiments are intended to be exemplary of the present invention for the purposes of providing and aiding a person skilled in the pertinent art to readily understand how to make and use the present invention.

Figure 1:
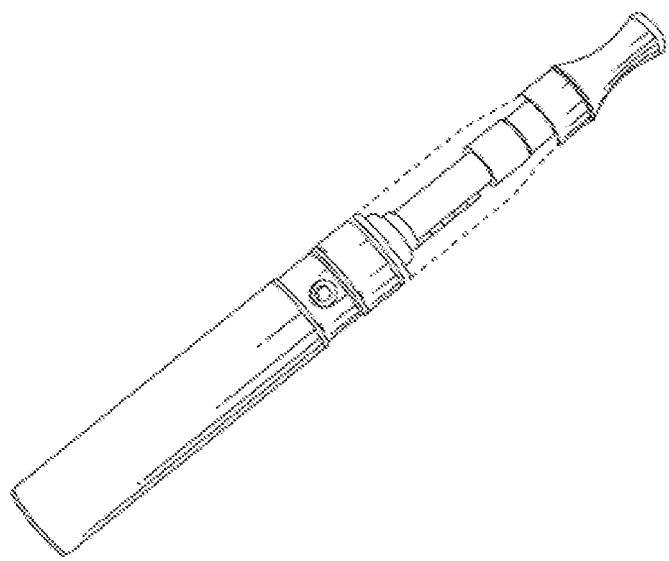
FIG. 1 illustrates a prior art electronic pen or cigarette.

FIG. 1 illustrates an electronic cigarette ("e-cigarette") or electronic pen which is commonly understood and known in the art. Depicted is a front end where the mouthpiece is, adjacent and operatively connected to the tank which contains e-liquid. The tank has a reservoir for e-liquid which is delivered to the coil, which when heated vaporizes the e-liquid. The vaporization process is supported by a sensor recognizing a change in pressure, communicating the same to some sort of printed circuit board or microprocessor which can connect the battery to heat the coil. As is illustrated, e-pens or e-cigarettes deliver vaporized e-liquid to a user through the mouthpiece. The vaporized e-liquid travels through a vapor port up to the mouthpiece and into the user's mouth and lungs.

Figure 2:
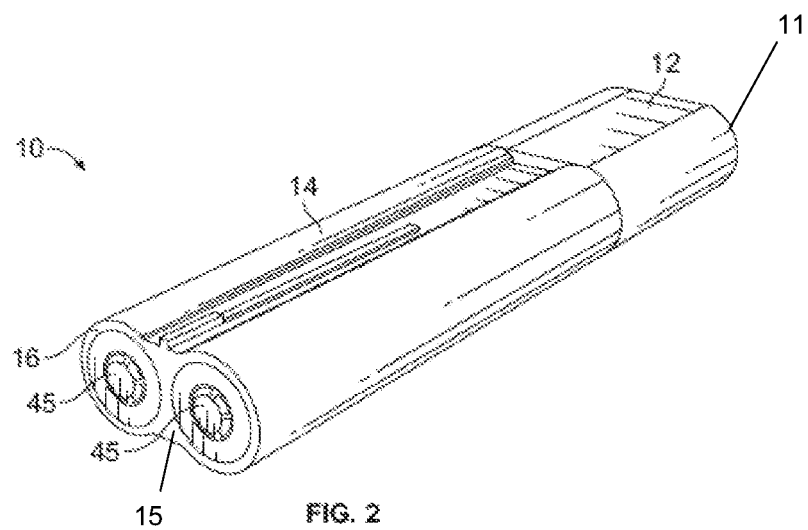
FIG. 2 illustrates an embodiment of the device in accordance with the principles of the present invention.

FIG. 2 illustrates a perspective view of one embodiment of the vaporization device 10 with a first end 11 having a mouthpiece 12 adjacent to a body 14 at a first end 11 of the body 14, and at a second end 15 of the body 14, the body 14 is adjacent to a ventilated end 16 on a second end 15 of the vaporization device 10 opposing the first end 11. The ventilated end 16 is provided with a plurality of airflow apertures 45 which can direct air flow through the vaporization device 10. Inside the body 14 of the device 10, unlike the pen or e-cigarette shown in FIG. 1, is housed at least two pens 18 which each have a battery and either threading compatible with retaining a tank 24 which has a vaporization chamber 26 and a coil 34 therein, or each pen can have a battery 22 plus a vaporization chamber 26 and a coil 34 wherein the vaporization chamber 26 can threadingly receive a tank 24 which has a reservoir containing e-liquid for vaporization (see e.g. FIG. 5). Once the tanks 24 having a vaporization chamber plus coil are appended to the pen battery 22, or tanks 24 appended to a battery 22 having also on the battery 22 a vaporization chamber 26 plus coil 34 when in use, the vaporization product produced from a vaporization event travels along a vapor port (not shown) through a mouthpiece aperture 42 (see e.g. FIG. 3) in the mouthpiece 12 to be drawn into a user's mouth and/or lungs. The mouthpiece aperture 42 can be any size that is effective for drawing vapor into the mouth of a user, and the mouthpiece 12 can be any shape and size that is ergonomically suitable for accommodating at least two pens 18 and a vapor port through which vaporization products are delivered from the plurality of vaporization chambers 26 to the mouthpiece aperture 42.

The first end 11 may comprise an internal biasing mechanism (not shown), for example, a spring, to hold internal components of the vaporization device 10 in place within the body 14 to protect against damaging the internal components if, for example, the vaporization device 10 is dropped, jarred, or shaken.

Preferably, the number of airflow apertures 45 is the same as the number of pens 18 (see e.g. FIG. 2 illustrating two pens and two airflow apertures 45) housed in the body 14. This allows for air to flow to each pen through the inside of the device, and also in an embodiment wherein each pen 18 is also provided with its own sensor 20, to direct air flow to each sensor 20 on each pen 18.

Figure 3:
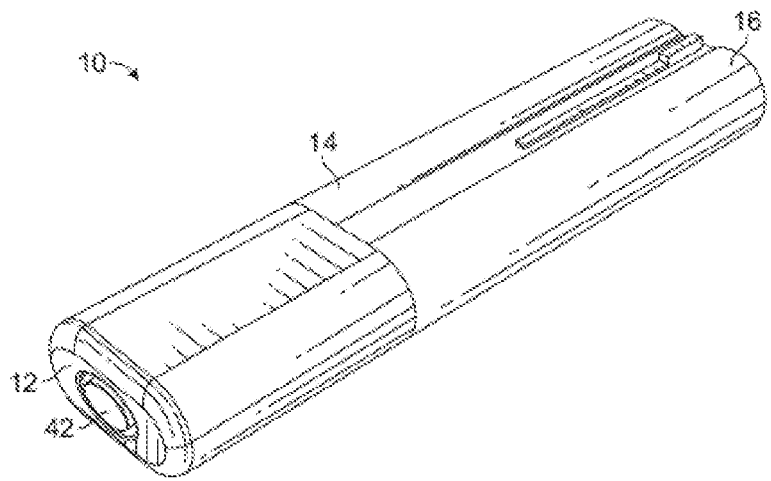
FIG. 3 illustrates an embodiment of the device in accordance with the principles of the present invention.

FIG. 3 provides another perspective view of the device 10 showing the mouthpiece 12, the body 14, and the ventilated end 16.

Figure 4:
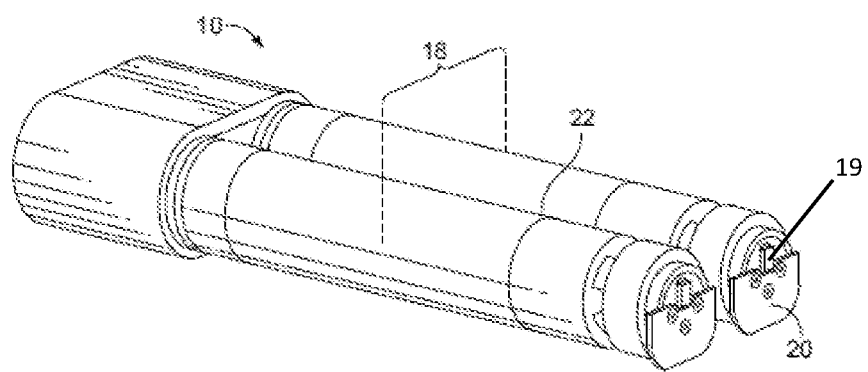
FIG. 4 illustrates an embodiment of the internal components of the body and the ventilated end of the device in accordance with the principles of the present invention.

FIG. 4 illustrates some of the internal components of the vaporization device 10. In this embodiment is shown that the vaporization device 10 is provided with at least two pens 18. Each pen 18 has its own printed circuit board ("PCB") 19, a sensor 20 for instance, but not limited to, a pressure sensor or an air-flow sensor 20, and a battery 22, which together control the vaporization of e-liquid components in the tank of the pens 18. The PCB 19 may include, for example, but is not limited to, a processing unit, a memory unit, a plurality of timers, and other suitable electrical components. Electronic components of the pen 18 are fixed to the PCB 19, which mechanically supports and electrically connects components of the assembly using tracks, pads, and other features etched from conductive sheets laminated onto a non-conductive substrate.

In some embodiments, the electronics of the PCB 19 are composed of a synthetic material that is thin and flexible. A thin and flexible PCB 19 allows the same to conform to the shape of the e-pen. The PCB 19 can be composed of materials such as, but not limited to, polyimide, polyethylene naphthalate, poletherimide, fluoropolymers, transparent conductive polyester, and other suitable materials for flexible electronics. In one embodiment, the PCB 19 is disposed inside the second end 15. In another embodiment the PCB 19 is configured to provide overvoltage protection to the batteries 22. In a further embodiment the PCB 19 is configured to transmit data regarding the charge level of the batteries 22, and the type and level of usage of the e-liquid.

Figure 5:
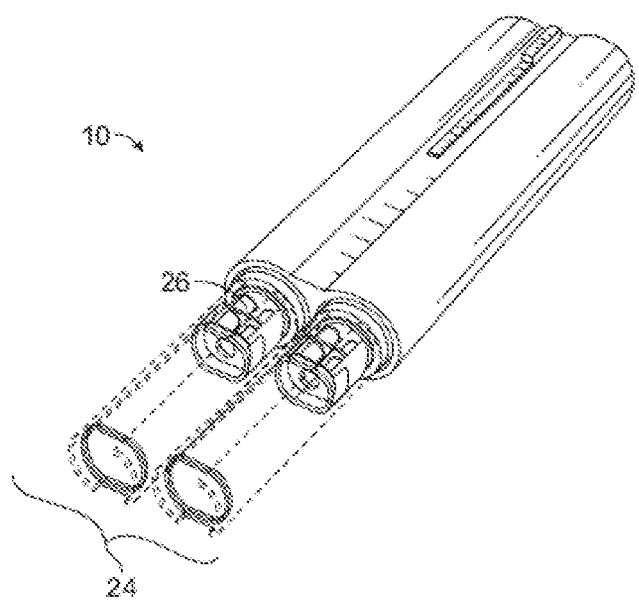
FIG. 5 illustrates an embodiment of the device in accordance with the principles of the present invention.

FIG. 5 illustrates the mouthpiece end of the vaporization device 10. In this particular embodiment, illustrated are two tanks 24 in which e-liquid is received in the reservoirs 28 (see e.g. FIG. 9) of each of the tanks 24. In this embodiment, each tank 24 is attached to a vaporization chamber 26 of each single pen 18. In this way, for each pen 18, a chamber 26 may vaporize a different e-liquid composition, be it an essential oil and/or nicotine and/or different strains of cannabis and/or different consistencies and percentages of PG, VG, and water, and/or essential oils, and can vaporize at a unique temperature apart from another pen of the plurality. This is accomplished by each pen 18 of the at least two pens being provided with a PCB 19, battery 22, and sensor 20 to specifically control the temperature and timing of vaporization of the e-liquid in the tank 24 of each pen 18 so as to most closely achieve an ideal vaporization temperature for the molecules in the e-liquid. The vaporization product from each of the vaporization chambers 26 can be mixed in a vapor port for inhalation through the mouthpiece aperture 42.

The battery 22 of the device 10 can be rechargeable, can be recharged/charged via induction charging, and/or can be charged by a wall electrical outlet, and/or by accommodating a USB to a computer to recharge/charge. In some embodiments, the battery 22 is a lithium battery, a lithium-ion battery, a nickel-cadmium ("NiCd") battery, a nickel-metal hydride ("NiMH") battery, or another suitable battery type. The battery 22 of each of the pens 18 will be of suitable shape and length to essentially provide the look and feel of an electronic cigarette. In the case of a rechargeable embodiment of the device 10, it is possible for a rechargeable device 10 to be provided with LED lights such that a pattern for charging is detected on the body 14 or the end 16. For example, but not limited to, a pattern whereby the LED lights flash in a pattern when the vaporization device 10 is being charged, and a different pattern when finished. The lights could also be on intermittently, steadily, or in a pattern when a vaporization event is activated, and in another embodiment could be activated, to demonstrate the amount of e-liquid remaining in each pen chamber, and in yet another embodiment be used to provide information for a user as to how charged (or speaking to the health of) the battery is in each pen.

When the battery is operationally affixed to the tank 24, and the user inhales, each of the pen sensors 20 communicates with the PCB and battery in order that the e-liquid in each of the tanks 24 is vaporized in the chamber 26 producing a vaporization product specific to the e-liquid which has been vaporized at the specific temperature dictated by the PCB of the particular pen 18. Thereafter, the vaporization product from each of the at least two pens 18 and thus e-liquids is mixed in the vapor port and inhaled through a single mouthpiece 12. In this way, the pleasure of a plurality of different e-liquid vaporization products can be attained in a single vaporization event and at a more effective temperature for each of the plurality of electronic cigarettes 18. This prevents over-heating, creating toxins and bad tastes, and allows for the most accurate and beneficial vaporization of targeted chemicals in each e-liquid, and the e-liquid itself considering essential oils, PG, VG, and mixes thereof, require different vaporization temperatures. For instance, by providing different vaporization temperatures across each of a plurality of pens 18, a VG heavy e-liquid needing to be vaporized at a higher temperature can be filled in a tank 24 which does not have a cotton wick, and paired with a tank carrying an e-liquid requiring a lower temperature and using a cotton wick, which is not recommended for vaporizing e-liquid which has high VG content. In this way, VG based e-liquid can be vaporized at a high temperature, without evaporating water while burning a cotton wick creating toxins, while at the same time vaporizing a different e-liquid requiring a lower temperature for producing a beneficial vaporization product.

In a disposable embodiment of the device 10, upon the final vaporization of the e-liquid in the reservoir the mouthpiece 12 can be immovably affixed to the body 14. In such an embodiment, the battery 22 need not be rechargeable, and the device in an embodiment may be provided with a window to visualize the e-liquid to know whether the e-liquid is finished.

In another embodiment, the device 10 is reusable, rechargeable, and the tanks replaceable. In such an embodiment, the mouthpiece 12 of the vaporization device 10 is removable, whereby the mouthpiece 12 is entirely removable, or preferably, moveably retained on the body 14 by for instance, but not limited to, a hinge, or a hook and loop, or a tie, whereby the mouthpiece 12 can be removed so as to reveal the replaceable tanks 24. When entirely removed, the mouthpiece 12 can be removably affixed to the body, for instance, but not limited to, a snap fit via a hook and groove accommodation. The mouthpiece 12 can also be configured to act as a circuit breaker such that when the mouthpiece 12 is not secured to the body 14, the battery circuit for vaporization is open and inoperable thus providing a safety feature for the device 10, for example for travel or when not in use. When the tanks 24 are operationally secured to the battery 22 and the pen 18, the mouthpiece 12 can be closed thus allowing the device 10 to be activated through a detected pressure change effecting the sensor and the PCB thus controlling vaporization.

In a reusable embodiment, the tanks 24 can be exchangeable/replaceable whereby a tank 24 can be disconnected from the pen 18 and another affixed thereto as desired. In this way, the user can have the pleasure of combining different vaporization products produced by different e-liquids in different tanks 24. In some embodiments, the disposable tank 24 is provided with a leak proof cap, which can be removably affixed thereto in order that after removal from the pen 18 there is no leakage from the tank 24. In this way, if a tank 24 still has e-liquid in the reservoir 28, the tank can be removed and reused, or another user can access the chamber 26 with a different tank 24, without disposing of the tank 24.

Different types of pen configurations can be used in the device 10. In one embodiment of the pen 18 of the device 10, the vaporization chamber 26 is affixed to the battery 22, and therefore, a tank 24 is received by the vaporization chamber plus coil 34 which is already affixed to the battery 22. In another embodiment of the pen 18 of the device 10, the tank includes both the reservoir 28 and the vaporization chamber 26 plus coil 28, and therefore, in such an embodiment the battery 22 threadingly receives the tank 24. In such an embodiment, once the e-liquid is depleted in the tank 24, the reservoir 28 plus vaporization chamber 26 including the coil 34 can be thrown away or at least removed, preferably capped, and set aside for later reuse without any leakage into the battery and other components of the pen 18.

In an embodiment wherein the tank 24 is disposable or can be interchanged or exchanged with another tank 24, remote technology, such as for instance blue tooth technology, on each pen 18 could be provided for programming temperature and time of vaporization for different tanks 24 based on the e-liquid composition, by and through the PCB, which may include memory, and would enable the remote storage of information regarding each tank containing e-liquid preferred vaporization temperature and vaporization time. The feature in this embodiment allows more particular control and/or personalization of a vaping experience whereby a user can retrieve or store information about each e-liquid and therefore mixtures of vaporization products including ideal temperatures of vaporization. It is also contemplated that this information and control be relayed and stored via a universal serial bus ("USB") or micro-USB connection to a computer. Furthermore, a microprocessor could be used to control, maintain, and change temperatures according to different e-liquid profiles in tanks 24.

Moreover, for a non-disposable embodiment whereby the battery can be recharged and the tanks 24 replaced/exchanged, it could be beneficial to monitor the temperature of the coil 34 in order to reach and maintain the temperature of the coil 34 and thus vaporize the desired components of the e-liquid. Therefore, a temperature sensor for reading and recording the temperature of the coil 34, temperature in the vaporization chamber 26, the temperature of the vaporization product, and/or the temperature of the e-liquid in the tank 24 could be included in the device 10. Temperature changes and recordings could also be presented in an LED screen located in the body 14 of the device 10.

In addition, a PCB 19 of the pen 18 of the device could be configured to store temperature information and/or to relay the same to a remote storage through blue tooth or remote technology. In this way, the temperature of the coil 34 of the device 10 could be more closely monitored and adjusted for more accurate vaporization.

Whether the device 10 itself is disposable or rechargeable/reusable, by providing a device 10 whereby tanks 24 containing different e-liquid components in the reservoirs that can be vaporized at the same time but at different temperatures, a customizable vaporization experience is obtainable by the vaporization device 10 according to a user's subjective tastes and experiences, or in the case of medical use, prescribed combinations.

Figure 6:
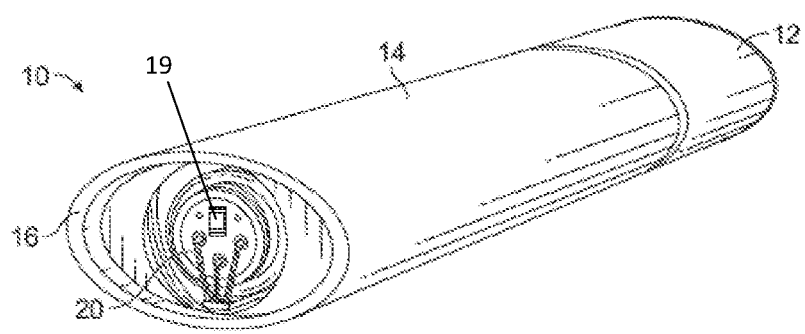
FIG. 6 illustrates an embodiment of the ventilated end of the device in accordance with the principles of the present invention.

In another embodiment, illustrated in FIG. 6, the ventilated end 16 has a single PCB 19 and sensor 20 whereby at least two pens 18 housed in the body 14 are controlled by the single PCB 19 and sensor 20, and preferably a microprocessor 30 which can control the temperature of each of the different pens 18 so that an appropriate vaporization temperature can be accommodated by each coil 34 for each tank 24 containing in its reservoir 28 a unique e-liquid. In an embodiment whereby the at least two pens 18 is controlled by a single PCB 19 and sensor 20, different tanks 24 which contain e-liquids of different viscosity than another tank's 24 e-liquid, and which are not combinable in a single tank 24, can still be vaporized at the same time.

Figure 9:
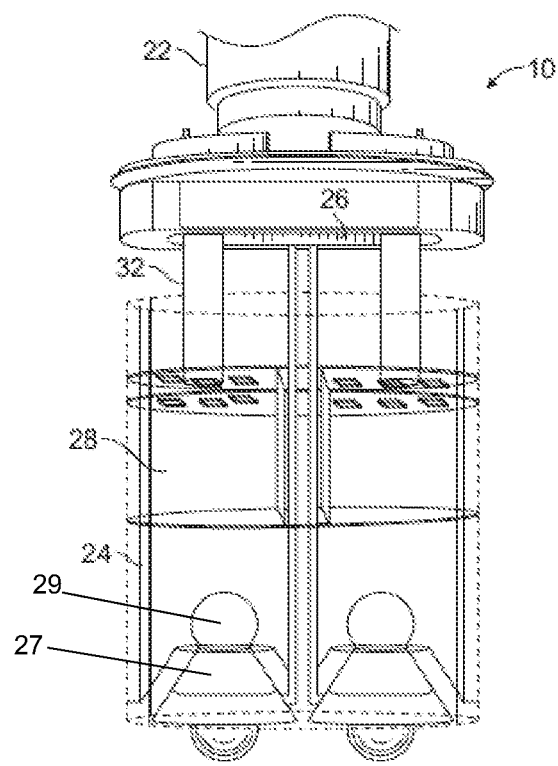
FIG. 9 illustrates an embodiment of a plurality reservoir tanks being assembled onto a battery of a pen of the device in accordance with the principles of the present invention.

In yet another embodiment, as in FIG. 9 a tank 24 is illustrated which being assembled onto a pen 18, whereby the tank 24 has a plurality of reservoirs 28 each for housing a different e-liquid. Although different e-liquids are provided in the tank 24, they are operationally connected to a single vaporization chamber 26. Though the advantage of mixing during vaporization is present in this embodiment, components of the e-liquid combination in the vaporization chamber 26 are vaporized all together at the same temperature. A molded reservoir plug 27, that can comprise a ball shaped end 29, caps the tanks 24 after the tanks 24 are filled to prevent tanks 24 from leaking or spilling. This embodiment also accommodates e-liquid which is not easily mixed due to the varying percentages of PG, VG, water, essential oils and/or other components, effecting viscosity. This embodiment also shows a dual wick 32 which allows for the delivery of e-liquid from each of the reservoirs 28 of the tank 24 to be delivered to the vaporization chamber 26 for vaporization at the same time and temperature. The battery 22 is also shown as pertaining to a single pen 18.

Figure 7:
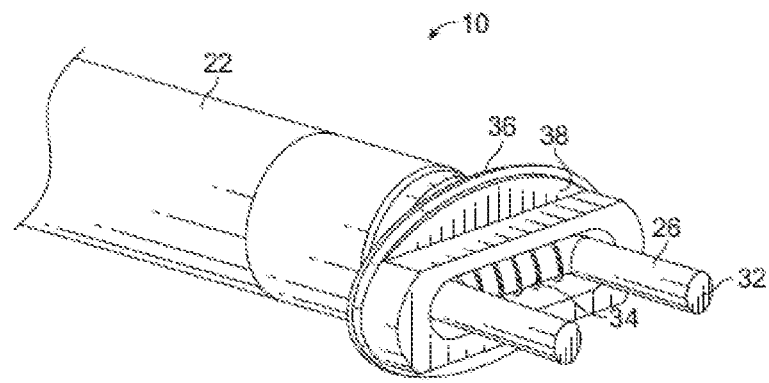
FIG. 7 illustrates an embodiment of the wick, coil and battery of the device in accordance with the principles of the present invention.

FIG. 7 illustrates a coil 34 of the device 10. In this embodiment, the dual wick 32 and coil 34 in the chamber 26 are visible. Also illustrated is a lip or O-ring 36 forming a lip to securely capture a corresponding groove on one or the plurality reservoir tank 28. In this way, the e-liquid in the tank 24 is less likely to be spilled because the tank 24 is secured on a wick body 38, and any jarring of the device 10 can reduce the chance of e-liquid leaking from the tank 24. In another configuration, the lip 36 can be on the tank 24 while the groove can be formed on the wick body 38. As described above, the coil 34 and vaporization chamber 26 can be contained within a disposable tank 24 whereby the tank 24 is threadingly received by the battery 22, or the coil 34 and the vaporization chamber 26 can be affixed to the battery 22 which is configured to threadingly receive a disposable tank 24 containing the e-liquid.

Figure 8:
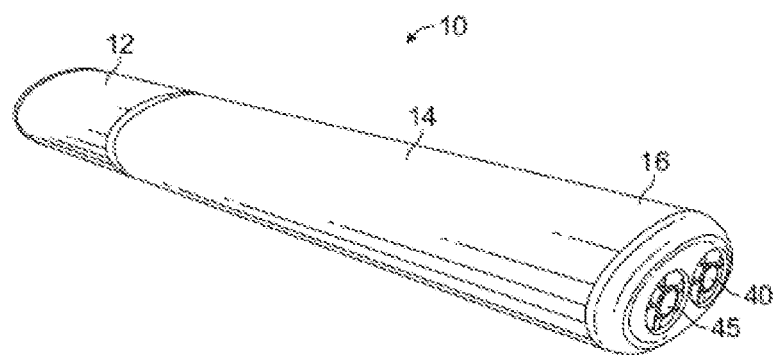
FIG. 8 illustrates an embodiment of the ventilated end showing a vortex tip of the device in accordance with the principles of the present invention.

FIG. 8 illustrates yet another embodiment of the device 10 whereby in the ventilated end 16 there is a vortex tip 40 for better air mixing through the air passage extending from the end 16 through the mouthpiece 12. In this particular embodiment, the body 14 is adjacent to and contiguous with the ventilated end 16 and is created as a single piece design. The body 14, and in this embodiment, the ventilated end 16, can be made of any material with heat dissipating properties including, for instance, but not limited to, aluminum and stainless steel, and also heat isolating materials that can reduce battery usage, provide heat dissipation properties, while at the same time isolate from the heat inside, such as for instance, but not limited to, plastics, or a combination of materials with heat dissipating and heat isolation properties. Moreover, for embodiments that have rechargeable batteries and disposable tanks, it is also contemplated that for the convenience of the user, a plurality of windows 44 (See FIG. 11) be provided in the body 14 in order to visualize the amount of e-liquid remaining in the plurality of tanks 24.

Figure 10:
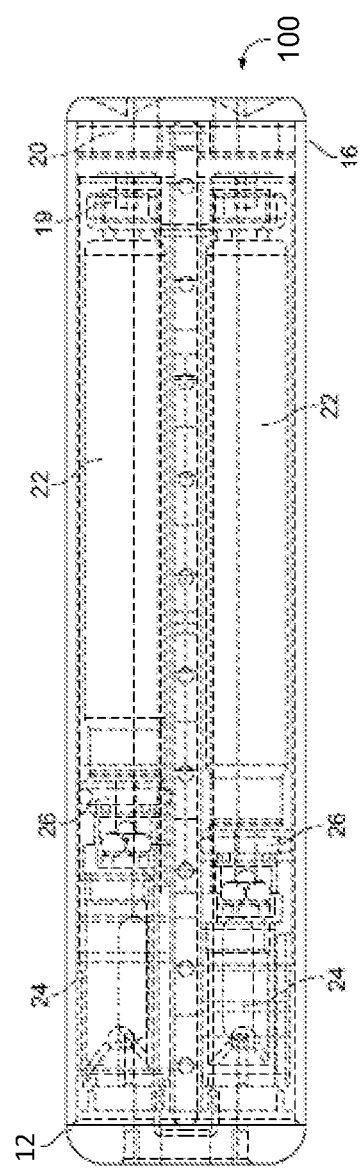
FIG. 10 illustrates a cross-section of an embodiment of the device from the mouthpiece to the ventilated end in accordance with the principles of the present invention.

FIG. 10 illustrates a cross-section of an embodiment of the vaporization device 100 in which there are two batteries 22, one for each of the pens 18, and the batteries 22 are different sizes. As discussed before, this is possible and is useful in embodiments where the e-liquid in the different tanks 24 is different and thus may require different voltages and different coils 34, leading to a need for different sized batteries 22 to most effectively vaporize the e-liquid in both tanks 24 at the same time over multiple vaporization events. The tanks 24 are capped with the molded reservoir plugs 27 comprising the ball shaped ends 29 (see FIG. 9). In some embodiments the coil 34 is constructed such that portions of the coil 34 can be energized as appropriate for vaporization of a particular e-liquid. For example, an entire coil 34 could be energized for maximum vapor production of a given e-liquid, or a portion of the coil 34 could be energized for application of lower temperatures to the given e-liquid or for a different e-liquid.

Figure 11:
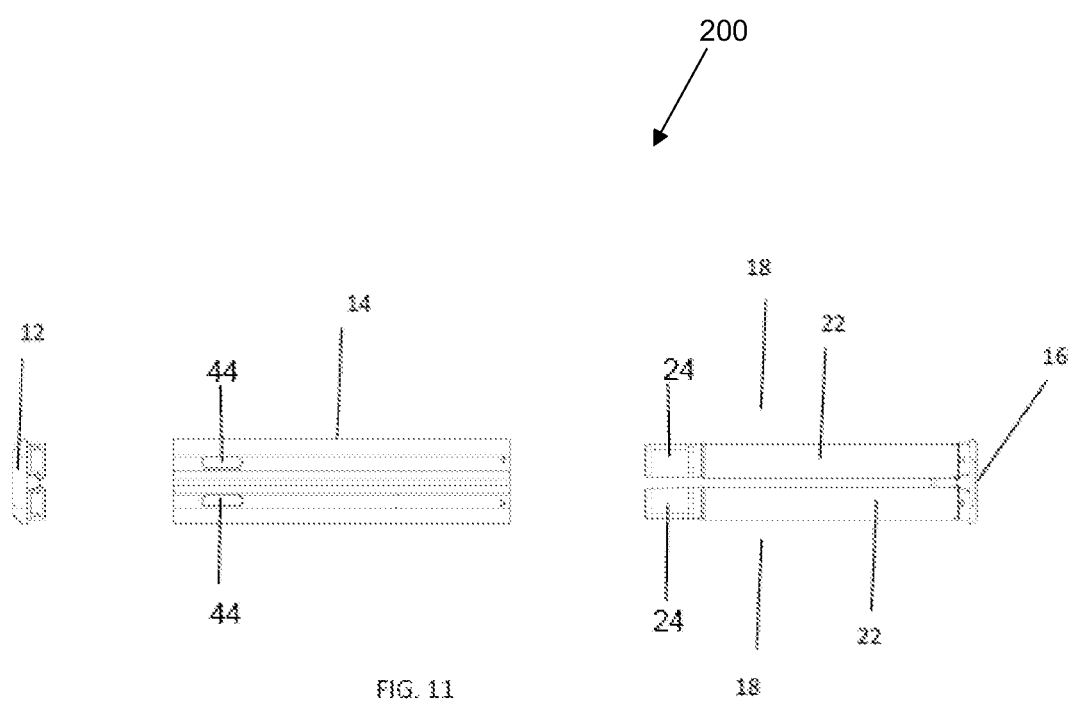
FIG. 11 illustrates an exploded view of an embodiment of the device in accordance with the principles of the present invention.

FIG. 11 illustrates an embodiment of the vaporization device 200 in an exploded view whereby it can be seen that the mouthpiece 12 is removable from the body 14 and so are the pens 18, potentially to change them or recharge them. In this embodiment, the plurality of windows 44 are located on the body 14 to allow for easy viewing of the amount of e-liquid in the tanks 24.

Referring to FIGS. 12 and 13, in yet another embodiment of the vaporization device 300 the second end 15 is a solid piece and does not comprise the ventilated end 16 of other embodiments. In this embodiment the second end 15 is removable from the body 14 and can be attached to the body using a clip 46. The clip 46 is pressed into a slot 48 to mechanically secure the second end 15 to the body 14. In some embodiments the clip 46 includes an eccentric cam that creates a press-fit within the slot 48 when the cam is rotated to secure the second end 15 onto the body 14. In other embodiments, the clip 46 includes an over-center type biased latch that snaps closed into the slot 48, where the latch may be a press-fit within the slot or the latch may include an extension that catches within a recess within the slot. In other embodiments, other mechanisms for a securing type latch as are known in the art may be used as the clip 46 in the current invention. In FIG. 12 the second end 15 is shown detached from the body 14 with the clip 46 in an open position. In FIG. 13 the second end 15 is shown attached to the body 14 and secured thereto by the clip 46 shown in a closed or locked position.

Figure 14:
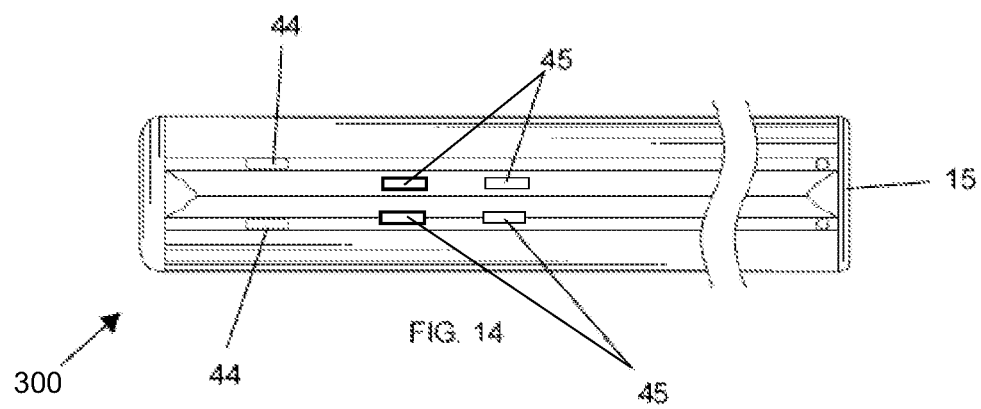
FIG. 14 illustrates a top view of an embodiment of the device in accordance with the principles of the present invention.

FIG. 14 illustrates a top view of an embodiment of the vaporization device 300 having a solid second end 15. In this embodiment, because the second end 15 is solid and does not allow air to flow through the vaporization device from the second end 15, the plurality of airflow apertures 45 are disposed through a wall of the body 14 of the vaporization device 10. The plurality of windows 44 allow for viewing of the level of e-liquid available in tanks 24 for vaporization.

Referring to FIG. 12, in one embodiment the second end 15 includes recesses (or small holes) 54 disposed on an engaging surface, and the body 14 includes inwardly extending bumps 56 that snap into the recesses 54 upon insertion of the second end 15 into the body 14. In another embodiment the bumps and the recesses could be reversed to achieve the same effect, where outwardly extending bumps 54a on the second end 15 snap into recesses 56a on an interior engaging surface of the body 14.

In another embodiment, the clip 46 can be used in combination with at least one magnet 58, for example, disposed near an open end of the slot 48 and/or on the clip 46 to ensure secure attachment of the second end 15 to the body 14. The secure and releasable attachment of the second end 15 to the body 14 allows for the internal components, such as the batteries 22 or tanks 24, for example, to be removed from the vaporization device 200, 300 for recharging and/or refilling.

Referring again to FIGS. 12 and 13, in one embodiment, a grip 50 releasably engages with the body 14. In one embodiment, the grip 50 can be adapted to releasably attach to a vaporization device that does not have a plurality of pens, for example, a vaporization device that comprises one pen. The grip 50, shown detached from the body 14 in FIG. 15, releasably attaches to the body 14, for example without limitation, singly or by any combination of a tongue and groove type connector, magnetically, adhesively, or by other releasable fastening means known in the art.

For example, in one embodiment lateral edges of a base of the grip 50 extend outwardly to engage with inwardly facing grooves on lateral sides of the slot 48. In this embodiment the lateral edges of the base of the grip 50 are slid into the open ends of the grooves to slide the grip 50 onto the base 14. In this embodiment the slot 48 (and the grooves on either lateral side of the slot 48) has a closed end providing a stop 60 for the grip 50 to rest against after it is seated within the slot 48 on the body 14.

Figure 15:
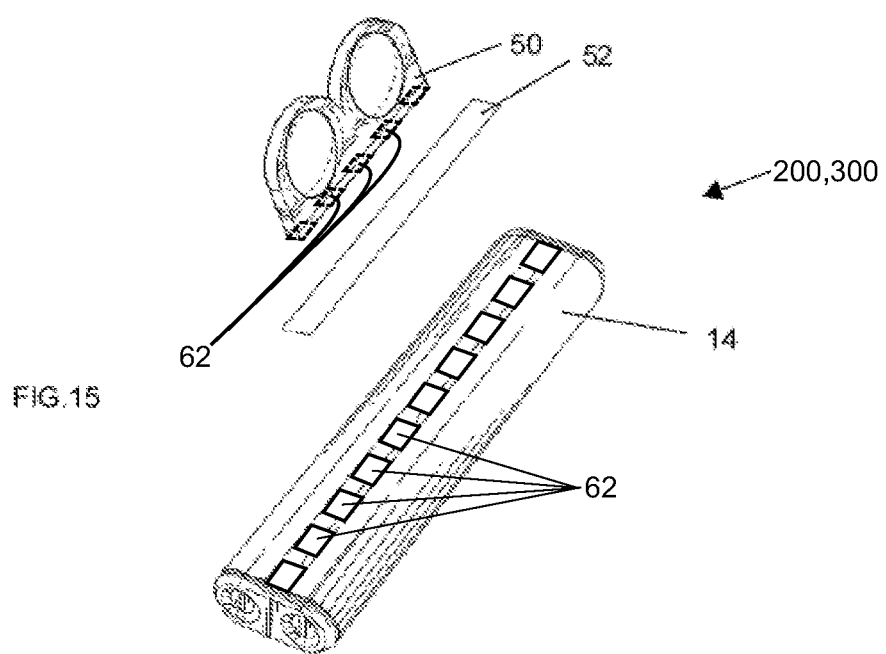
FIG. 15 illustrates a bottom view of an embodiment of the device in accordance with the principles of the present invention.

As illustrated in FIG. 15, in another embodiment of the vaporization device 400, the grip 50 magnetically engages the body 14 via a plurality of thin magnets 62 disposed on the base of the grip 50 and/or disposed on the body 14. The number of magnets in the plurality of thin magnets, for example, ranges from 10 to 35, preferably from 15-30, and even more preferably from 20-30. The body 14 can be made of a ferrous metal, for example, steel.

In another embodiment, the magnets 62 are disposed on the body 14 along the slot 48 (see FIGS. 12 and 13). In a further embodiment, the magnets 62 disposed on the grip 50 and/or on the body 14 have alternating facing polarity from magnet to magnet such that, for example, a first magnet would present a South polarity, the next magnet would present a North polarity, the following magnet would again present a South polarity, and so forth. Such an arrangement of alternating poles on both the grip 50 and the body 14 provides a positioning mechanism for the grip 50 on the body 14 because the grip 50 would be magnetically held only in positions where opposite polarity magnets are directly facing one another.

In another embodiment as illustrated in FIG. 15, the grip 50 engages the body 14 using an adhesive strip fastener 52. The body 14 could comprise a slot 48 in this embodiment. The adhesive strip fastener 52 can comprise a permanent glue, a nonpermanent glue, be a magnetic adhesive type strip, or a combination thereof. In one embodiment, one side of the adhesive strip comprises a different type of adhesive than the other side of the adhesive strip. In one embodiment, the adhesive strip fastener is accommodated on the body 14 within the slot 48 (see FIGS. 12 and 13).

INDUSTRIAL APPLICABILITY

The vaporization device includes a body configured to house a plurality of vaporization pens in a cavity inside the body. The pens can have batteries of different sizes to accommodate the power requirements for heating various e-liquids. A grip releasably attaches to a bottom surface of the body. The grip can be attached magnetically, adhesively, or by a sliding tongue in groove arrangement. Ends of the body are removable to allow access to the pens disposed inside.

Numerous modifications to the present invention will be apparent to those skilled in the art in view of the foregoing description. It is not desired to limit the invention to the exact construction and operation shown and described, and accordingly, all suitable modifications and equivalents may be resorted to, falling within the scope of the invention. Accordingly, this description is to be construed as illustrative only of the principles of the invention and is presented for the purpose of enabling those skilled in the art to make and use the invention and to teach the best mode of carrying out same. The exclusive rights to all modifications which come within the scope of the appended claims are reserved. All patents, patent publications and applications, and other references cited herein are incorporated by reference herein in their entirety.

I claim:

1. A vaporization device comprising:
a body configured to house at least one vaporization pen in a cavity inside the body;
the body comprising a bottom surface and a top surface;
a grip having an elongate base, wherein the grip releasably attaches to the bottom surface of the body via the elongate base, and wherein a releasable attachment between the elongate base and the body is selected from the group consisting of a plurality of magnets disposed on one or both of the grip and the body, adhesive on one or both of the grip and the body, and combinations thereof.

2. The vaporization device of claim 1, wherein the grip is attached to the bottom surface using a plurality of magnets disposed on the grip.

3. The vaporization device of claim 2, where the plurality of magnets comprises 10 to 35 magnets.

4. The vaporization device of claim 3, where the plurality of magnets comprises 15 to 30 magnets.

5. The vaporization device of claim 4, where the plurality of magnets comprises 20 to 30 magnets.

6. The vaporization device of claim 1, wherein the grip is attached to the bottom surface using a first plurality of magnets disposed on the grip and a second plurality of magnets disposed on the body, and wherein both pluralities of magnets have alternating facing polarities.

7. The vaporization device of claim 1, wherein the grip is attached to the bottom surface using an adhesive.

8. The vaporization device of claim 1, further comprising an elongate recess disposed into the bottom surface wherein the elongate base is accommodated within the recess.

9. A vaporization device comprising:
a body configured to house at least one vaporization pen having a battery;
a mouthpiece adjacent and contiguous with a first end of the body;
a second end of the body opposite the mouthpiece, where the second end of the body is removable from the body to allow access to an interior of the body; wherein
the second end attaches to the body using a clip that presses into a slot on the body; and wherein
the body includes a magnet that cooperates with the material of the clip to secure the clip in a closed position.

10. The vaporization device of claim 9, wherein the second end is solid and a plurality of airflow apertures is disposed through a wall of the body.

11. The vaporization device of claim 9, wherein the mouthpiece is removable from the body to allow access to an interior of the body.

12. A vaporization device comprising:
a body configured to house at least one vaporization pen in a cavity inside the body;
the body comprising a bottom surface and a top surface;
an elongate recess disposed into the bottom surface, the elongate recess including opposing lateral grooves that extend from long sides of the elongate recess into the body;
a grip having an elongate base, wherein lateral edges of opposing long sides of the elongate base are accommodated by the opposing lateral grooves to releasably attach the grip to the body.

* * * * *